United States Patent [19]

Wason

[11] 4,159,280
[45] Jun. 26, 1979

[54] THERAPEUTIC DENTIFRICES IN UNLINED CONTAINER AND METHODS

[75] Inventor: Satish K. Wason, Churchville, Md.

[73] Assignee: J. M. Huber Corporation, Locust, N.J.

[21] Appl. No.: 826,901

[22] Filed: Aug. 24, 1977

Related U.S. Application Data

[63] Continuation-in-part of Ser. No. 723,345, Sep. 15, 1976, abandoned.

[51] Int. Cl.$^2$ .................. A61K 7/18; B65D 81/24; B65D 81/26; B65D 85/14
[52] U.S. Cl. ............................ 206/524.4; 424/52
[58] Field of Search ................ 424/52; 206/524.4

[56] References Cited

U.S. PATENT DOCUMENTS

| | | | |
|---|---|---|---|
| 3,095,356 | 6/1963 | Moss | 424/57 |
| 3,122,483 | 2/1964 | Rosenthal | 424/49 |
| 3,689,637 | 9/1972 | Pader | 424/52 |
| 3,699,221 | 10/1972 | Schole et al. | 424/54 |
| 3,728,446 | 4/1973 | Roberts et al. | 424/49 |
| 3,842,168 | 10/1974 | Colodney | 424/52 |
| 3,864,470 | 2/1975 | Watson | 424/49 |
| 3,893,840 | 7/1975 | Wason | 106/288 B |
| 3,906,090 | 9/1975 | Colodney | 424/52 |
| 3,911,104 | 10/1975 | Harrison | 424/52 |
| 3,928,541 | 12/1975 | Wason | 423/339 |
| 3,934,000 | 1/1976 | Barth | 424/49 |
| 3,937,321 | 2/1976 | Delaney et al. | 206/84 |
| 3,939,262 | 2/1976 | Kim | 424/52 |
| 3,991,177 | 11/1976 | Vidra et al. | 424/50 |
| 4,007,260 | 2/1977 | Kim | 424/52 |
| 4,024,239 | 5/1977 | Pader | 424/57 |
| 4,038,380 | 7/1977 | Cordon | 424/49 |

FOREIGN PATENT DOCUMENTS

| | | |
|---|---|---|
| 2428037 | 1/1975 | Fed. Rep. of Germany. |
| 1344043 | 1/1974 | United Kingdom. |
| 1384375 | 2/1975 | United Kingdom. |
| 1408922 | 10/1975 | United Kingdom. |
| 1473305 | 5/1977 | United Kingdom. |
| 1506045 | 4/1978 | United Kingdom. |

OTHER PUBLICATIONS

Degussa Technical Bulletin Pigments No. 9 "Synthetic Products for Toothpastes" 12 pp. (1970).
Degussa Technical Bulletin No. 49 "Aerosil ® in Pharmaceuticals and Cosmetics" reprint from Drugs made in Germany, vol. 13, pp. 47–58, 108–117 (1970), p. 3, part 3.7 Preventing Corrosion-Toothpaste Tubes.

*Primary Examiner*—Shep K. Rose
*Attorney, Agent, or Firm*—Robert L. Price; Harold H. Flanders

[57] ABSTRACT

The corrosion and staining of unlined aluminum tube surfaces by dentifrices such as toothpastes, particularly when the dentifrices contain therapeutic agents, is substantially prevented by incorporation into the dentifrice of a controlled amount of an alkaline earth metal ion such as calcium ion, in the range of 0.005–0.2 weight percent, and preferably in the range of 0.005–0.070 weight percent of the dentifrice. The alkaline earth metal may be provided from any water soluble alkaline earth metal salt or as a reaction product of the alkaline earth metal salt with an amorphous silica abrasive and/or thickener.

18 Claims, No Drawings

THERAPEUTIC DENTIFRICES IN UNLINED CONTAINER AND METHODS

CROSS-REFERENCE TO RELATED APPLICATIONS

This is a continuation-in-part of parent application Ser. No. 723,345, filed Sept. 15, 1976 now abandoned.

BACKGROUND OF THE INVENTION

1. Field of the Invention

The present invention relates to dentifrice compositions and more particularly to dentifrice compositions such as toothpastes containing therapeutic agents and/or polishing agents and other ingredients, wherein the composition also contains a controlled amount of alkaline earth metal ion to prevent corrosion and staining when placed in unlined aluminum tubes over extended periods of storage.

2. Description of the Prior Art

Broadly speaking, there are two types of modern day dentifrices on the market which may be described as opaque and clear-gel dentifrice compositions.

Each type of above mentioned dentifrice is marketed under two different versions:
A. Cosmetic Type
B. Therapeutic Type A cosmetic type toothpaste is one which contains no fluoride and is promoted for whitening and brightening of the teeth. A therapeutic toothpaste, however, contains fluoride as anti-caries agent.

Therapeutic dentifrice compositions such as toothpastes, normally contain a fluoride therapeutic agent such as stannous fluoride, monofluorophosphate, or derivatives thereof, as well as polishing agents, humectants, and other materials. These compositions are usually placed in aluminum or plastic tubes for sale on the commercial market. It is usually preferred to use aluminum tubes but it has been discovered that when such toothpaste compositions contain a therapeutic fluoride compound, a reaction with the interior of the unlined aluminum tube takes place so that staining and other corrosive action occurs apparently because of some reaction or incompatibility between the bare aluminum surface and one or more of the materials in the toothpaste. This incompatibility appears in the form of gas production, swelling of the tube, corrosion, and black stains on the inside surface of unlined aluminum container. Accordingly, the standard practice in the marketing of therapeutic toothpastes today has been to line the aluminum tube with a plastic, lacquer or other material, which therefore substantially adds to the cost of packaging and marketing the toothpaste.

Many prior art attempts have been made to solve this problem because unlined aluminum tubes are much more economical to use and are generally lighter in weight than the lined tubes. For example, U.S. Pat. Nos. 3,662,060 and 3,624,199 disclose compositions which are said to overcome this problem. Further, U.S. Pat. No. 3,678,155 discloses that monofluorophosphate ions prevent corrosion of unlacquered aluminum tubes when the toothpaste contains milled alpha-alumina trihydrates as an abrasive. Also U.S. Pat. No. 3,864,471 discloses a dentifrice composition containing a monofluorophosphate and a polishing agent containing alkaline earth metal carbonate and insoluble alkali metal phosphate, alumina or mixture thereof, to minimize corrosion in unlined aluminum containers.

SUMMARY OF THE INVENTION

It is accordingly an object of the present invention to overcome or otherwise mitigate these problems of the prior art.

It is a further object of this invention to provide a novel toothpaste composition which will not stain or otherwise corrode unlined tubes, a novel abrasive for use in such toothpastes, and provide a method for the preparation and packaging of a toothpaste composition in unlined tubes which will not cause corrosion and staining problems on the interior of the tube.

A still further object of the invention is to provide a non-corrosive therapeutic toothpaste composition which contains a controlled amount of alkaline earth metal ion so that the resulting composition can be placed in and marketed in unlined aluminum tubes.

Other objects and advantages of the present invention will become apparent as the description thereof proceeds.

In satisfaction of the foregoing objects and advantages there is provided by this invention a therapeutic dentifrice composition comprising a fluoride-containing therapeutic agent, a polishing agent, a liquid phase, and about 0.005 to 0.20 weight percent of alkaline earth metal ion per 100 parts of the toothpaste composition. Also provided is a novel polishing agent which can supply the alkaline earth metal ions. There is also provided by this invention an unlined aluminum tube containing a dentifrice composition comprising a fluoride-containing therapeutic agent, a polishing agent, a liquid phase, and about 0.005 to 0.20 parts of alkaline earth metal per 100 parts of toothpaste composition. There is further provided by this invention a method for inhibiting the staining and corrosion of unlined aluminum tubes by toothpaste compositions containing fluorides which comprises the incorporation within said toothpaste composition of about 0.005 to 0.20 parts of alkaline earth metal per 100 parts by weight of said toothpaste composition.

DESCRIPTION OF PREFERRED EMBODIMENTS

As pointed out above, since the introduction of therapeutic-containing dentifrice compositions, it has not been possible to produce a commercially usable product which could be packaged in unlined aluminum tubes because of the incompatibility problems between the aluminum surface of the tube and the other components of the dentifrice, particularly the fluorides. While substantial work has been carried out in an effort to overcome this problem as indicated by the prior art discussed above, problems in this area still persist. The present invention overcomes problems of this type in a commercially viable manner and provides a fluoride-containing dentifrice or toothpaste composition which can be packaged and sold in unlined aluminum tubes.

According to the present invention, it has been discovered that the problem of corrosion of unlined aluminum tubes when formulated with a therapeutic dentifrice composition can be overcome by incorporation within the toothpaste composition of a controlled amount of an alkaline earth metal . The alkaline earth metal with which this invention is primarily concerned is especially calcium, but there also may be used magnesium or strontium. Calcium is preferred because of its ready availability, inexpensiveness and ease of incorporation into the dentifrice. The metal may be incorporated into the dentifrice or toothpaste mixture in any substantially water soluble form such as the nitrate, oxide, hydroxide or chloride. The most preferred materials for incorporation into the therapeutic dentifrice compositions of this invention include calcium nitrate, calcium oxide, calcium hydroxide, and calcium chloride. It should also be noted however, that organic salts such as calcium acetate, calcium formate and the like may also be used. Corresponding strontium and magnesium salts may also be used. The only limitations to be placed on the alkaline earth metal salt are that it be substantially soluble, not cause any problems of safety in the compositions, and remain available to combat corrosion.

There are of course dentifrice and other toothpaste compositions known in the art which contain calcium salts in substantial amounts, as taught for example in U.S. Pat. No. 3,864,471 which contains 40-50% of calcium carbonate and U.S. Pat. No. 3,624,199 which contains 20-75% calcium carbonate. However, calcium carbonate is generally insoluble, and is not effective to inhibit corrosion of the tube. Therefore, an important aspect of the present invention resides in the carefully controlled amount of water-soluble alkaline earth ion which is incorporated into the toothpaste composition. According to the present invention, the controlled amount of alkaline earth metal ion which is present must be sufficient to be effective and available to prevent corrosion but yet insufficient to stoichiometrically interfere with fluoride availability in the toothpaste. According to the present invention, it has been found that the amount of alkaline earth metal which must be present to prevent corrosion is at least about 50 parts per million, or 0.005 weight percent, and not more than about 2000 parts per million, or 0.02 weight percent, should be present to avoid interference with fluoride availability. Therefore, the amount of alkaline earth metal which should be present should range from about 50-2000 parts per million or 0.005 to 0.02 weight percent based on the toothpaste.

As pointed out above, the alkaline earth metal ion may be incorporated into the toothpaste as any water soluble salt. However, it is also within the scope of the present invention to supply the alkaline earth metal ion in combination with silica and silicate type abrasive and/or polishing agents. According to one aspect of this embodiment, a controlled structure, amorphous precipitated silica may be incorporated into the therapeutic composition in sufficient amounts to supply the necessary alkaline earth metal, such as calcium ion, to overcome the problems of corrosion and staining. These dentifrice grade controlled structure precipitated silicas contain calcium ions on the silica surface of the precipitated silica abrasive, polishing agent or thickening agent.

The dentifrice grade controlled structure precipitated silicas or silicon dioxides referred to above are novel products available from the J. M. Huber Corporation and are silicon dioxide products of the type described for example in my U.S. Pat. Nos. 3,960,586 and 3,928,541 which have been treated with an alkaline earth metal salt to provide the alkaline earth metal ions in the composition. The products described in these patents are precipitated silicic acid or silicon dioxide pigments which are prepared by the acidulation of an alkali metal silicate such as sodium silicate and an acid such as sulfuric acid, in the presence of a salt or electrolyte such as sodium sulfate. The precipitated silicas resulting from the reaction wherein the sulfate is a necessary reactant in the process may be described as sulfate liquor products. After preparation of the precipitated silica in wet cake form, and washing, it is then reslurried in water and treated with a soluble alkaline earth metal salt such as calcium hydroxide, calcium oxide, calcium nitrate, or calcium chloride, in sufficient amounts to incorporate the necessary amount of alkaline earth metal ions directly into the silica. The reaction of silica with alkaline earth metal is conducted at ambient temperature and with agitation. The amount of alkaline earth metal ions introduced will be sufficient to provide the required amount of alkaline earth metal ions in the toothpaste but is correlated with any desired amount of alkaline earth metal ions incorporated directly into the toothpaste composition.

It will be understood therefore that the amorphous silica material is pretreated with the critical level of alkaline earth metal material and then incorporated into the toothpaste composition in the requisite amounts as desired. These silica compositions provide good cleaning properties at RDA values of between 200-400. (RDA-Grabbenstetter et al, Jour. of Dental Research, 37, 1060, 1958).

The precipitated silicon dioxides of the present invention are preferably prepared by charging a 3-15 weight percent aqueous solution of alkali metal sulfate, preferably sodium sulfate, to a reactor and adding a solution of an alkali meatl silicate solution, preferably a sodium silicate solution, to the reactor to achieve a pH of about 8-10.4. This results in pre-polymerization of the alkali metal silicate. The aqueous sodium silicate solution should have a silicate concentration range of about 10-25 weight percent, and more preferably 18 to 22 weight percent, and a composition of $Na_2O.2.6\ SiO_2$ for best results. The aqueous solution is then raised to a temperature of about 66° to 83° C. (150° to 180° F.) and with continuous agitation the solution is acidulated by the addition of an aqueous solution of a mineral acid having a concentration of about 10-25 weight percent at a substantially constant pH in the range of about 8.0 to 10.4. Preferably the mineral acid and alkali metal silicate are added simultaneously as described in my U.S. Pat. No. 3,960,586. For purposes of preparation of the basic precipitated silica or silicon dioxide, the disclosures of my prior U.S. Pat. Nos. 3,960,586 and 3,928,541 are expressly incorporated herein by reference. The mineral acid is preferably sulfuric acid as sulfuric acid provides best results but as known in the art as in my prior U.S. Pat. No. 3,960,586, other acidulation agents such as nitric acid, phosphoric acid, hydrochloric acid, carbonic acid and the like may also be employed. The time period over which the alkali metal silicate and/or sulfuric acid are added to the reactor can be predetermined and is generally based on the volume of the reactor and the difficulties in control on the volume of the reactor and the difficulties in control of the temperature and agitation. After completion of the additions, the acidulation acid is continued to be added until the pH of the slurry falls below about 6.0 and preferably in the range of about 4.8-5.0. The resulting slurry is the precipitated silicon dioxide contained in the reaction medium.

After the pH of below 6.0 is obtained, the slurry is then heated for a digestion period of 10 to 30 minutes at a temperature of 10° to 30° C. above the reaction temperature and the reaction pH again adjusted as necessary. The resulting slurry is then filtered and washed with additional water to remove any reaction by-product such as sodium sulfate which may be contained in the silicon dioxide product.

In the process of the present invention, at the point of filtration and washing of the silicon dioxide wet cake, the material is then subjected to treatment with alkaline earth metal ions to produce the new abrasive products of the present invention. In accordance with the process of the present invention, the wet wash filter cake is then reslurried in its own water or with the addition of fresh water at ambient temperature with agitation. While under agitation, this slurry is then treated with sufficient alkaline earth metal ions and preferably calcium ions, in the form of substantially soluble salt to provide sufficient alkaline earth metal ions corresponding to provide about 30 to 2000 parts per million, intimately associated with the silicon dioxide, this amount being based on 100 parts of dentifrice. The amount of alkaline earth metal ions added is based on the total weight of the dry product contained in the wet cake form, that is recoverable solid. Since the amount of abrasive may vary in dentifrice compositions, the amount of alkaline earth metal salt will also be varied.

The alkaline earth metal ion added at this point is preferably calcium ion because of its readily availability, inexpensiveness and ease of incorporation into the silicon dioxide. The calcium ions may be incorporated into the silicon dioxide at this stage in any substantially water soluble form such as the nitrate, oxide, hydroxide, or chloride, but lime or calcium hydroxide is preferred. Food grade salts should be used. By soluble salt is meant that any reasonably soluble salt of calcium may be used since it is only necessary to provide extremely small amounts of the calcium ions to the mixture. Also, organic salts such as calcium acetate, calcium formate, and the like may also be used. The corresponding strontium and magnesium salts of the alkaline earth class may also be used. The only limitations to be placed on the alkaline earth metal salt to be added are that it be sufficiently water soluble to provide the ions, not present any problems of safety in the resulting toothpaste compositions, and be effective to provide the necessary fluoride compatibility.

After treatment with the alkaline earth metal ion, the cake slurry is then agitated vigorously for 10–20 minutes, preferably 15 minutes, to provide the effective level of alkaline earth metal for treatment on the surface of the silicon dioxide abrasive. The resulting product is then filtered, spray dried, preferably at an inlet temperature of 483° C. (900° F.) and outlet temperature of 122° C. (250° F.) as known in the art, and subsequently milled to the desired degree of fineness.

The precipitated amorphous silicas which are preferably used in this embodiment may be characterized by the following combinations of properties:

Oil Absorption-Rub-Out Method (cc/100 g)=80–120
BET Surface Area ($m^2/g$)=75–325
MSA Average Aggregate Size (micron)=1–10
Bulk Density (lbs./cu.ft.)=10–30

It is also to be understood however, that the invention includes other types of silica polishing agents including Xerogels as described in U.S. Pat. No. 3,538,230. Commercially available Xerogels such as Syloid 63, manufactured by Davison Division of W. R. Grace & Co., can be utilized when incorporated with controlled amounts of calcium ion or alkaline earth metal ions or pretreated with calcium ion or alkaline earth metal ions, as described herein. It is also to be understood that sodium aluminosilicate polishing agents can be formulated in therapeutic compositions according to this invention when the sodium aluminosilicate materials are combined with the critical amounts of alkaline earth metal as described herein.

As known in the art, a dentifrice may contain; e.g., humectant materials and binders to give the dentifrice a smooth texture and good flowability. The specific formulations of toothpastes are well known in the art and are disclosed for example in U.S. Pat. Nos. 2,994,642 and 2,538,230 and numerous publications. A further detailed disclosure of dentifrice formulations is given in U.S. Pat. No. 3,726,961.

In this regard, dentifrice formulations have been produced, ranging from liquids and powders to the highly popular pastes or dental creams. Dental creams are the most difficult to compound successfully in that they require careful balancing of polishing agent, humectant, water, binder, preservatives, detergents, flavoring, sweeteners, and therapeutic agents to produce a smooth homogeneous paste.

Most dental cream formulations use one of several conventional phosphate materials as the polishing agent. Examples of the phosphate polishing agents are dicalcium phosphate, anhydrous dicalcium phosphate, tricalcium phosphate, thermally converted dicalcium phosphate, and insoluble sodium metaphosphate. The amount of phosphate materials added to the dental formulations will range between about 5 percent and 60 percent by weight.

The most widely used humectants in toothpaste are glycerine and sorbitol. Propylene glycol is also used in small amounts and to a very limited extent. The primary function of humectant as part of the liquid phase is to retain moisture which provides good texture and maintains an attractive glossy appearance when the paste is exposed to air.

The binder employed therein is to prevent separation of the liquid and solid phases. The most conventionally used binders are the seaweed colloids and synthetic derivatives of cellulose, specifically Carrageenan and sodium carboxymethyl cellulose. Others such as gums have been used. Combinations of these binders have also been employed.

Since the natural and synthetic water dispersions of organic binders are subjected to microbial or mold attack, a relatively small amount of preservatives is added to the paste. Examples of preservatives used in the industry are the esters of parahydroxyl benzoates.

The function of the detergents within the dental formulation is to provide greater cleansing action due to the lowering of the surface tension and the sudsing action in the mouth. Among detergents used are sodium N-lauryl sarcosinate, sodium lauryl sulfate, sulfoculaurate, sodium alkyl sulfoacetate, and sodium dioctyl sulfosuccinate.

Since toothpaste flavoring probably represents the greatest single factor in consumer acceptance, great care has been employed in selecting balanced blends of different essential oils. These are rarely, if ever, used alone. Combinations of principal flavors are wintergreen, peppermint, and sassafras, and are used with secondary oils such as pimento, clove and anise.

Saccharin and sodium cyclamate are widely used to improve taste and enhance the flavor qualities of the toothpaste. The synthetic sweeteners may be used in combination to obtain optimum sweetness and absence of after-taste. Their desirable properties are obtained at very low concentrations and consequently they have negligible influence on the toothpaste consistency.

Since water is such a common element, it is important in obtaining stable toothpaste formulations to employ substantially pure water therein. It is common practice to demineralize the water that is employed.

It is also within the scope of the invention to provide the proper amount of alkaline earth metal within the dentifrice composition by pretreating the water with the calcium or alkaline earth metal so that the water used can serve as the alkaline earth metal source.

The invention is operable with respect to any of the therapeutic agents now being used in therapeutic dentifrice compositions including the alkali metal fluorides such as sodium fluoride, sodium monofluorophosphate, stannous fluoride, and the like, all of which are well known.

In general, such dentifrice compositions will normally contain about 5-50 wt% of polishing agent, up to about 1 wt% of fluoride-containing therapeutic agent, about 30-40 wt. % deionized water, and the remainder being liquid phase carrier materials such as glycerin, sorbitol and the like. As indicated above, according to the present invention, the composition will also contain from 0.005 up to 0.20 parts of alkaline earth metal ion, preferably calcium ion, based on the toothpaste composition. It has been found that this amount of alkaline earth metal is sufficient to overcome problems with staining and corrosion of unlined aluminum tubes, but is insufficient to interfere with the fluoride availability in the paste and thus not interfere with the therapeutic action of the dentifrice composition.

With respect to incorporation of the controlled amount of alkaline earth metal in the compositions of the present invention, it is to be noted that in Degussa Technical Bulletin No. 9, there is a disclosure of an "Aerosil 200" polishing agent for use in chalk toothpastes, and it is pointed out on page 8 of this Bulletin that in toothpastes containing the cheaper polishing agent, chalk, the use of "Aerosil 200" is worthwhile to the extent that the less expensive unlacquered aluminum tubes can be used since corrosion protection for unlacquered aluminum tubes is by formation of minute quantities of insoluble calcium silicate from this composition. A minimum of 1% of "Aerosil 200" is required. However at page 8 of the same Bulletin, it is stated that even with the use of "Aerosil", it is not possible to attain effective corrosion protection for nontreated aluminum tubes when the toothpaste compositions contain fluorine in the form of monofluorosodium phosphate. However, this reference does teach on page 8, that when 3-5 weight percent of Light Hydrated Alumina W-16 is incorporated into the fluoride-containing toothpaste, corrosion protection can be obtained. Contrary to the teachings of this Technical Bulletin, it has been discovered according to the present invention that fluorine-containing toothpastes can be placed in unlined aluminum tubes if there is placed therein a controlled amount of alkaline earth metal ion.

In consideration of the incorporation of silica type products in the dentifrice composition of the present invention, it will be understood that all silica products and raw materials have incidental amounts of calcium present. For example, trade publications covering the Xerogels sold as Syloid 63 indicate the presence of 0.01% calcium as calcium oxide. This corresponds to 0.007% calcium or up to 70 parts per million in Syloid 63. However, since only about up to 35 weight percent levels of the silica products can be incorporated into toothpaste compositions, this indicates that inherently, the resulting dentifrices can contain only 0.0035 of calcium oxide or 25 ppm of calcium, an insufficient amount for corrosion protection. It will also be noted that the precipitated silicas of J. M. Huber Corporation as described above, have a tendency to pick-up or react with calcium ions which make these products extremely attractive for combination with the correct amount of calcium ions and incorporation into toothpastes since the silicas also provide excellent abrasion properties for toothpaste compositions.

The silica abrasives described herein are used at loadings of about 15-30 wt % in the dentifrice. Therefore they should contain a minimum of 168 ppm calcium at 30 wt % and 336 ppm at 15 wt % to provide minimum amounts of calcium. However, they can also contain up to about 7000 ppm or more.

The following specific examples are further illustrative of the nature of the present invention, but it is to be understood that the invention is not limited thereto. The compositions are prepared in the conventional manner and all amounts of the various ingredients are by weight unless otherwise specified. In the following examples and throughout the specification parts are by weight unless otherwise indicated.

EXAMPLES

In the following examples the toothpaste compositions were prepared and compared with commercial products or controls. In evaluating the toothpaste compositions, a chart was used to rate the interior tube wall to determine the presence or absence of staining and corrosion. As basis for the chart, each composition was prepared and then aged at 49° C. for nine weeks. The percentage of soluble fluoride ion and tube compatibility data were determined periodically during the nine-week storage stability period. In this examination, each three weeks under the aging conditions (49° C.) corresponds to about one year aging at room temperature. During the studies, the unlined tubes containing the compositions were opened periodically and examined for any staining/corrosion on the tube interior wall. The following legend was used for rating the tube properties of the compositions:

| Rating | Tube Interior Wall |
|---|---|
| 10 | No air on wall, no discoloration on wall |
| 8-9 | No air on wall, light gray stain on wall |
| 6-7 | Air on wall, light gray stain on wall |
| 4-5 | Air on wall, gray stain on wall |
| 2-3 | Air on wall, dark grey stain on wall |
| 1 | Air on wall, black stain with pitting of wall |

In all of the following examples, the alkaline earth metal was calcium and was added as soluble calcium nitrate to provide the amount of calcium indicated in each composition.

EXAMPLES 1-4

Dentifrice Compositions in Which Calcium Was Added to the Toothpaste

The following dentifrice compositions were prepared with a low structure silica polishing agent and a known level of calcium was added to the composition to provide tube compatibility properties.

|  | Examples 1-4 Composition | | | |
|---|---|---|---|---|
|  | 1 | 2 | 3 | 4 |
| Sodium monofluorophosphate | 0.76 | 0.76 | 0.76 | 0.76 |
| Low Structure silica | 30.00* | 29.970 | 29.941 | 29.587 |
| Calcium as water soluble $Ca(NO_3)_2 \cdot 4H_2O$** | 0.00 | 0.0295 | 0.059 | 0.413 |
| Glycerine | 23.00 | 23.00 | 23.00 | 23.00 |
| Sodium carboxymethyl-cellulose | 1.30 | 1.30 | 1.30 | 1.30 |
| Hydrated alumina | 1.00 | 1.00 | 1.00 | 1.00 |
| Sodium lauryl sulfate | 2.00 | 2.00 | 2.00 | 2.00 |
| Sodium benzoate | 0.50 | 0.50 | 0.50 | 0.50 |
| Sodium Saccharin | 0.20 | 0.20 | 0.20 | 0.20 |
| Flavor | 0.90 | 0.90 | 0.90 | 0.90 |
| Water (deionized) | Balance | Balance | Balance | Balance |
| Total | 100.00 | 100.00 | 100.00 | 100.00 |

*low structure silica containing 5 ppm calcium
**The conversion factor for calcium nitrate . $4H_2O$ to calcium is 5.9. The molecular weight of $Ca(NO_3)_2 \cdot 4H_2O$ is 236. The atomic weight of calcium is 40. Therefore 236 parts of calcium nitrate . $4H_2O$ provide 40 parts of calcium ion, or 236/40 or 5.9 parts of calcium nitrate . $4H_2O$, which corresponds to one part of calcium.

In compositions 2, 3, and 4, calcium nitrate . $4H_2O$ was added in the dentifrice composition which corresponds to calcium level of 0.0295/5.9 or 50 ppm (0.005%); 100 ppm (0.01%) and 700 ppm (0.07%), respectively. The tube compatibility data for these Examples are set forth in following Table 1.

TABLE 1
Rating of Tube Properties - 49° C. Aging Study

| Composition | Weeks | | | | |
|---|---|---|---|---|---|
|  | 0 | 1 | 3 | 6 | 9 |
| 1 | 10 | 4 | 3 | 3 | 1 |
| 2 | 10 | 10 | 10 | 10 | 10 |
| 3 | 10 | 10 | 10 | 10 | 10 |
| 4 | 10 | 10 | 10 | 10 | 10 |

It is clear from above data that composition 1 was unacceptable in tube compatibility properties because it did not contain the minimum critical level of calcium in the therapeutic dentifrice composition.

EXAMPLES 5-8

The following dentifrice compositions were prepared wherein the content of sodium monofluorophosphate in each is equivalent to 0.1% fluoride ion.

| Composition | Parts | | | |
|---|---|---|---|---|
| Sodium monofluoro-phosphate | 0.76 | 0.76 | 0.76 | 0.76 |
| Low Structure silica | 30.00(A) | 30.00(B) | 30.00(C) | 30.00(D) |
| Glycerine | 23.00 | 23.00 | 23.00 | 23.00 |
| Sodium carboxymethyl-cellulose | 1.30 | 1.30 | 1.30 | 1.30 |
| Hydrated alumina | 1.00 | 1.00 | 1.00 | 1.00 |
| Sodium lauryl sulfate | 2.00 | 2.00 | 2.00 | 2.00 |
| Sodium benzoate | 0.50 | 0.50 | 0.50 | 0.50 |
| Sodium saccharin | 0.20 | 0.20 | 0.20 | 0.20 |
| Flavor | 0.90 | 0.90 | 0.90 | 0.90 |
| Water (deionized) | 40.34 | 40.34 | 40.34 | 40.34 |
| Total | 100.00 | 100.00 | 100.00 | 100.00 |

(A) low structure silica of composition 5 contained 5 ppm calcium
(B) low structure silica of composition 6 contained 168 ppm calcium
(C) low structure silica of composition 7 contained 406 ppm calcium
(D) low structure silica of composition 8 contained 688 ppm calcium The low structure silicas employed in Examples 5, 6, 7 and 8 were characterized by the following combination of properties:

Oil Absorption—Rub-Out Method (cc/100 mg) = 80–120
BET Surface Area ($m^2/g$) = 75–325
MSA Average Aggregate Size (microns) = 1–10
Bulk Density (pounds/cu.ft.) = 10–30

The calcium treated low structure silicas of compositions 5, 6, 7 and 8 were prepared by the following procedure:

Dry sodium sulfate was added to 10.0 gallons of water in a 200 gallon reactor so that the sodium sulfate concentration in the reaction medium was 10%. The pH of the reaction medium was then adjusted to 9.0 by the addition of sodium silicate. The reaction temperature was 65° C. (150° F.). The sodium silicate solution had an $SiO_2 \cdot Na_2O$ mole ratio of 2.5 and a concentration of 2.0 pounds per gallon. Sodium silicate was added to the reaction medium for 4 minutes. At this point the sodium silicate addition was stopped and sulfuric acid of 11.4% concentration was added to the reaction medium until the pH of 9.0 was reached. At this point the sodium silicate solution and the sulfuric acid solution was added simultaneously for a period of 35 minutes. At the end of the 35 minute period of silicate addition, the silicate was discontinued and the acid addition was continued until a slurry pH of 5.5 was obtained. The batch was digested at 77° C. (170° F.) for 20 minutes and the resulting wet cake recovered and washed.

The wet cake was then divided into four separate portions and treated by the following procedure.

Each batch of wet wash filter cake was then reslurried without water addition at ambient temperature with agitation. While under agitation, the slurry was treated with sufficient Codex grade (U.S. purity food grade) hydrated lime (calcium hydroxide) to provide the amount of calcium ion treatment described in compositions 5, 6, 7 and 8. The amount of calcium hydroxide was based on the weight of dry recoverable solid product in the wet cake form. After treatment with the calcium ion, the cake slurry was agitated vigorously for 15 minutes to provide the effective level of calcium ion treatment on the surface of the silicon dioxide abrasive. Each resulting product is then spray dried at an inlet temperature of 483° C. and outlet temperature of 122° C. milled and characterized.

Compositions 5, 6, 7 and 8 were aged at 49° C. for nine weeks and tube compatibility data were determined periodically during the nine-week storage stability period. The results for tube compatibility properties are listed below in Table 2.

TABLE 2

Rating of Tube Properties - 49° C. Aging Study

| Composition | Weeks | | | | |
|---|---|---|---|---|---|
| | 0 | 1 | 3 | 6 | 9 |
| 5 | 10 | 4 | 3 | 3 | 1 |
| 6 | 10 | 10 | 10 | 10 | 10 |
| 7 | 10 | 10 | 10 | 10 | 10 |
| 8 | 10 | 10 | 10 | 10 | 10 |

It will be noted from Table 2 that dentifrice composition 5 caused a severe degree of black stain and pitting on the tube wall after nine weeks of aging study. Compositions 6, 7 and 8 were stable and showed excellent tube compatibility properties. Thus, it is very clear that when a silica polishing agent contains a minimum critical level of calcium, it does not corrode the unlined aluminum tubes.

EXAMPLES 9-11

Stabilization of Xerogel Therapeutic Dentifrices with Calcium

Therapeutic dentifrices were prepared with xerogel polishing agents. All compositions contained a known level of calcium ions (added as water soluble calcium nitrate) except composition 9. The compositions were prepared in the conventional manner and packaged in unlined aluminum tubes. All amounts of the various ingredients were by weight unless otherwise specified.

The following dentifrice compositions were prepared. The content of sodium monofluorophosphate in each was equivalent to 0.1% fluoride ion.

| Composition | Parts | | |
|---|---|---|---|
| | 9 | 10 | 11 |
| Glycerine (99.5% solution) | 22.00 | 22.00 | 22.00 |
| Sodium benzoate | 0.50 | 0.50 | 0.50 |
| Sodium saccharin | 0.20 | 0.20 | 0.20 |
| CMC - 7 MF | 1.00 | 1.00 | 1.00 |
| Sodium monofluorophosphate | 0.76 | 0.76 | 0.76 |
| Water (deionized) | 36.54 | 36.54 | 36.54 |
| Xerogel (Syloid 63) | 35.00 | 34.82 | 34.70 |
| Hydrated alumina | 1.00 | 1.00 | 1.00 |
| $TiO_2$ | 0.50 | 0.50 | 0.50 |
| Sodium lauryl sulfate | 1.50 | 1.50 | 1.50 |
| Calcium nitrate . $4H_2O$* | 0.00 | 0.18 | 0.30 |
| Flavor | 1.00 | 1.00 | 1.00 |

*0.18% and 0.30% calcium nitrate . $4H_2O$ in compositions 10 and 11 correspond to 0.18/5.9 or 0.03% calcium (300 ppm calcium) and 0.30/5.9 or 0.05% calcium (500 ppm calcium)

It will be noted that the composition of Example 9 did not contain any calcium. The tube properties were then determined when the dentifrices were aged at 49° C. for nine weeks and were rated at intervals of 1, 3, 6, and 9 weeks. The following Table 3 shows the degree of corrosion or staining of the unlined aluminum tubes.

TABLE 3

Tube Compatibility Properties - 49° C. Aging Study

| Composition | Weeks | | | | |
|---|---|---|---|---|---|
| | 0 | 1 | 3 | 6 | 9 |
| 9 | 10 | 7 | 6 | 6 | 5 |
| 10 | 10 | 10 | 10 | 10 | 10 |
| 11 | 10 | 10 | 10 | 10 | 10 |

From the data in Table 3 it is clear that the compositions of Examples 10 and 11 exhibit excellent tube compatibility properties. Note that rating of 10 means no discoloration of the unlined tube container. Since composition 9 did not contain the critical level of calcium, the tube compatibility properties were found to be unacceptable after nine weeks storage at 49° C.

According to the suppliers bulletin, the Xerogel, Syloid 63, has the following properties:

| | |
|---|---|
| Loss on ignition | 6.5 |
| 5% slurry pH | 4.1 |
| % $SiO_2$ ignited basis | 99.5 |
| Particle size, microns | 9.0 |
| Surface area, $m^2/g$ | 625 |
| Oil absorption, #/100 lb | 60 |
| Bulk density, pounds/cu. ft. | 29 |

In addition to above properties, Syloid 63 has the following chemical composition (from supplier's bulletin):

| Chemical Analysis (dry basis) | % |
|---|---|
| Aluminum as $Al_2O_3$ | 0.04 |
| Titanium as $TiO_2$ | 0.03 |
| Calcium as CaO | 0.01 |
| Sodium as $Na_2O$ | 0.02 |
| Zirconium as $ZrO_2$ | 0.01 |
| Trace element (oxides) | 0.02 |

EXAMPLE 12

Effect of Calcium on Commercial Toothpastes

"Aim" clear-gel therapeutic toothpaste is packaged in a lined container to prevent corrosion and staining of tube interior wall.

"Colgate Dental Cream" (CDC) is also packaged in a lined container to avoid the corrosion and staining of the tube interior wall.

To check the effectiveness of calcium addition in solving the tube compatibility problem, both "Aim" and "CDC" were purchased from the supermarket and each paste was divided into three parts.

"Aim" toothpaste was divided in parts A, B, and C. Part A was packaged in an unlined aluminum tube without any addition of calcium to the toothpaste. Parts B and C were mixed with a known level of calcium and then packaged in unlined aluminum tubes.

"CDC" (Colgate Dental Cream) was also divided into three parts D, E, and F. Part D was packaged in an unlined aluminum tube without the addition of any calcium. To parts E and F, a known level of calcium was added. The data obtained with "Aim" and "CDC" compositions packaged in unlined containers are listed in Table 6 and the compositions for each are as follows:

EXAMPLE 12

| Composition | % Calcium (3) | Commercial % Dentifrice | |
|---|---|---|---|
| A | 0.00 | 100.00 | (1) |
| B | 0.10 | 99.41 | (1) |
| C | 0.16 | 99.16 | (1) |
| D | 0.00 | 100.00 | (2) |
| E | 0.10 | 99.41 | (2) |
| F | 0.16 | 99.16 | (2) |

(1) Aim toothpaste, purchased from supermarket
(2) Colgate Dental Cream, purchased from supermarket
(3) Added as $Ca(NO_3)_2$ . $4H_2O$

TABLE 4

Tube Compatibility Properties - 49° C. Aging Study

| Composition | Weeks | | | |
|---|---|---|---|---|
| | 1 | 3 | 6 | 9 |
| A | 5 | 4 | 3 | 1 |
| B | 10 | 10 | 10 | 10 |
| C | 10 | 10 | 10 | 10 |
| D | 5 | 5 | 4 | 2 |
| E | 10 | 10 | 10 | 10 |
| F | 10 | 10 | 10 | 10 |

Compositions B, C, E and F have excellent tube compatibility properties when compared with compositions A and D. The addition of the calcium thus helped stabilize these therapeutic dentifrice compositions.

EXAMPLES 13–17

The following dentifrice compositions were prepared to illustrate the use of sodium aluminosilicates (SAS) as polishing agents. The composition of Example 13 was used as a control in which no calcium was added. Known amounts of calcium were added to the compositions of Examples 13, 15, 16 and 17. The compositions were as follows:

| Composition | Parts | | | | |
|---|---|---|---|---|---|
| | 13 | 14 | 15 | 16 | 17 |
| Glycerine (99.5%) | 22.00 | 22.00 | 26.00 | 25.00 | 30.00 |
| Sodium benzoate | 0.50 | 0.50 | 0.50 | 0.50 | 0.50 |
| Sodium saccharin | 0.20 | 0.20 | 0.20 | 0.20 | 0.20 |
| CMC - 7 MF | 1.00 | 1.00 | 1.00 | 1.00 | 1.00 |
| Sodium monofluorophosphate | 0.76 | 0.76 | 0.76 | 0.76 | 0.76 |
| Calcium nitrate . 4H$_2$O* | 0.00 | 0.20 | 0.20 | 0.20 | 0.24 |
| Deionized water | 36.54 | 36.34 | 39.54 | 38.54 | 43.30 |
| SAS Polishing agent | 35.00(A) | 35.00(A) | 27.80(B) | 29.80(C) | 20.00(D) |
| Hydrated alumina | 1.00 | 1.00 | 1.00 | 1.00 | 1.00 |
| TiO$_2$ | 0.50 | 0.50 | 0.50 | 0.50 | 0.50 |
| Sodium lauryl sulfate | 1.50 | 1.50 | 1.50 | 1.50 | 1.50 |
| Flavor | 1.00 | 1.00 | 1.00 | 1.00 | 1.00 |

*Note that in compositions 14, 15 and 16, 0.2% Ca(NO$_3$)$_2$ . 4H$_2$O corresponds to 0.03% calcium ion and 0.24% Ca(NO$_3$)$_2$ . 4H$_2$O in composition 17 corresponds to 0.04% calcium ion.
(A) The SAS product used in compositions 13 and 14 has a SiO$_2$/Al$_2$O$_3$ ratio of 11.0
(B) The SAS product used in composition 15 has a SiO$_2$/Al$_2$O$_3$ ratio of 2.5
(C) The SAS product used in composition 16 has a SiO$_2$/Al$_2$O$_3$ ratio of 130
(D) The SAS product used in composition 17 has a SiO$_2$/Al$_2$O$_3$ ratio of 400

The preferred sodium aluminosilicates (SAS) have the following molar chemical composition:

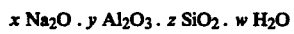

$x$ Na$_2$O . $y$ Al$_2$O$_3$ . $z$ SiO$_2$ . $w$ H$_2$O wherein
x denotes the moles of Na$_2$O
y denotes the moles of Al$_2$O$_3$
z denotes the moles of SiO$_2$
w denotes the moles of water When y is fixed at 1, the value of z corresponds to the silica/alumina molar ratio of SAS. The low structure SAS abrasives and polishing agents have a silica/alumino ratio or z values of 2.5 to 400.

The properties of SAS polishing agents are:
Oil Absorption, Rub-Out Method (cc/100 g)=75–125
BET Surface Area (m$^2$/g)=50–300
MSA Average Aggregate Size (microns)=1–10
Bulk Density (pounds/cu.ft.)=12–35

Compositions 13 through 17 were aged at 49° C. for nine weeks and the tube compatibility properties were evaluated at intervals of 1, 3, 6, and 9 weeks and the results are shown in the following Table 5.

TABLE 5

Tube Compatibility Properties, 49° C.

| Composition | Weeks | | | |
|---|---|---|---|---|
| | 1 | 3 | 6 | 9 |
| 13 | 1 | 1 | 1 | 1 |
| 14 | 10 | 10 | 10 | 10 |
| 15 | 10 | 10 | 10 | 10 |
| 16 | 10 | 10 | 10 | 10 |
| 17 | 10 | 10 | 10 | 10 |

Note that compositions 14 through 17 have excellent tube compatibility properties.

What is claimed is:

1. An article of manufacture comprising an unlined aluminum tube which is normally subject to corrosion and staining by prolonged contact with a toothpaste composition contacting a fluoride therapeutic agent, said unlined aluminum tube containing a toothpaste composition comprising a fluoride therapeutic agent, a solid phase, a liquid phase, and a fluoride corrosion and staining preventing amount of an alkaline earth metal, said amount being about 0.005 to 0.20 weight percent, and said alkaline earth metal being provided as the reaction product of a water soluble alkaline earth metal salt with an amorphous silica.

2. The article of manufacture of claim 1, wherein the fluoride therapeutic agent is selected from the group consisting of monofluorosodium phosphate, sodium fluoride, stannous fluoride, and mixtures thereof.

3. The article of manufacture of claim 1, wherein said alkaline earth metal is selected from the group consisting of calcium, magnesium, strontium, and mixtures thereof.

4. The article of manufacture of claim 1, wherein said amount of the alkaline earth metal is about 0.005 to 0.070 weight percent.

5. The article of manufacture of claim 1, wherein said amorphous silica is selected from the group consisting of amorphous precipitated silica, sodium aluminosilicates, silica xero-gels, and mixtures thereof.

6. The article of manufacture of claim 1, wherein said amorphous silica is an amorphous precipitated silica having the following properties:
Oil Absorption-Rub-Out Method (cc/100 g)=80–120
BET Surface Area (m$^2$/g)=75–325

MSA Average Aggregate Size (microns)=1-10
Bulk Density (lbs./cu.ft.)=10-30

7. The article of manufacture of claim 1, wherein the alkaline earth metal is calcium.

8. The article of manufacture of claim 7, wherein said calcium is provided by a water soluble calcium salt selected from the group consisting of calcium nitrate, calcium oxide, calcium hydroxide, calcium fluoride, calcium acetate and calcium formate.

9. The article of manufacture of claim 8, wherein said calcium salt is selected from the group consisting of calcium nitrate, calcium oxide, calcium hydroxide and calcium fluoride.

10. A method for preventing the corrosion and staining of an unlined aluminum tube which is normally subject to corrosion and staining by prolonged contact with a toothpaste composition containing a fluoride therapeutic agent, said method comprising incorporating into said toothpaste composition a fluoride corrosion and staining preventing amount of an alkaline earth metal, said amount being about 0.005 to 0.20 weight percent, and said alkaline earth metal being provided as the reaction product of an alkaline earth metal salt with an amorphous silica; said toothpaste composition comprising the fluoride therapeutic agent, a liquid phase and a solid phase.

11. The method of claim 10, wherein the fluoride therapeutic agent is selected from the group consisting of monofluorosodium phosphate, sodium fluoride, stannous fluoride, and mixtures thereof.

12. The method of claim 10, wherein said alkaline earth metal is selected from the group consisting of calcium, magnesium, strontium, and mixtures thereof.

13. The method of claim 10, wherein said amount of the alkaline earth metal is about 0.005 to 0.070 weight percent.

14. The method of claim 10, wherein said amorphous silica is selected from the group consisting of amorphous precipitated silica, sodium aluminosilicates, silica xerogels, and mixtures thereof.

15. The method of claim 10, wherein said amorphous silica is an amorphous precipitated silica having the following properties:
Oil Absorption-Rub-Out Method (cc/100 g)=80-120
BET Surface Area (m$^2$/g)=75-325
MSA Average Aggregate Size (microns)=1-10
Bulk Density lbs./cu.ft.)=10-30

16. The method of claim 10, wherein the alkaline earth metal is calcium.

17. The method of claim 16, wherein said calcium is provided by a water soluble calcium salt selected from the group consisting of calcium nitrate, calcium oxide, calcium hydroxide, calcium fluoride, calcium acetate and calcium formate.

18. The method of claim 17, wherein said calcium salt is selected from the group consisting of calcium nitrate, calcium oxide, calcium hydroxide and calcium fluoride.

* * * * *

UNITED STATES PATENT OFFICE
CERTIFICATE OF CORRECTION

PATENT NO. : 4,159,280

DATED : June 26, 1979

INVENTOR(S) : Satish K. Wason

It is certified that error appears in the above-identified patent and that said Letters Patent are hereby corrected as shown below:

Column 3, line 35, "0.02" should be --0.2--

Column 3, line 39, "0.02" should be --0.2--

Column 7, line 25, "parts" should be --weight percent--

Column 15, line 14, "fluoride" should be --chloride--

Column 16, line 29, "fluoride" should be --chloride--.

Signed and Sealed this

Second Day of December 1980

[SEAL]

Attest:

SIDNEY A. DIAMOND

Attesting Officer

Commissioner of Patents and Trademarks